(12) United States Patent
Mitchell

(10) Patent No.: US 7,348,033 B1
(45) Date of Patent: Mar. 25, 2008

(54) COLD-REMEDY FOOD SUPPLEMENT FOR SIMULTANEOUSLY LOWERING BLOOD PRESSURE AND SUSTAINING BLOOD SUGAR

(76) Inventor: Horace Mitchell, 10530 Envoy St., Houston, TX (US) 77016

( * ) Notice: Subject to any disclaimer, the term of this patent is extended or adjusted under 35 U.S.C. 154(b) by 0 days.

(21) Appl. No.: 11/607,679

(22) Filed: Dec. 1, 2006

Related U.S. Application Data

(60) Provisional application No. 60/819,682, filed on Jul. 10, 2006.

(51) Int. Cl.
*A61K 36/8962* (2006.01)
*A61K 36/81* (2006.01)
*A61K 36/736* (2006.01)
*A61K 36/752* (2006.01)

(52) U.S. Cl. .................. 424/754; 424/760; 424/735; 424/736

(58) Field of Classification Search ............... None
See application file for complete search history.

(56) References Cited

U.S. PATENT DOCUMENTS 6,641,801 B1 * 11/2003 Brown .................. 424/49

2007/0134299 A1 * 6/2007 Giles .................. 424/440
2007/0141229 A1 * 6/2007 Bonsall .................. 426/650

FOREIGN PATENT DOCUMENTS

CA 1086557 A * 9/1980
CN 1243717 A * 2/2000

* cited by examiner

*Primary Examiner*—Christopher R. Tate
*Assistant Examiner*—Heather L Anderson
(74) *Attorney, Agent, or Firm*—Harrison Law Office

(57) ABSTRACT

Dietary food supplement compositions which promote the ability to quell adverse common cold symptoms while simultaneously reducing blood pressure and sustaining blood sugar equilibrium. Food supplement compositions comprising specially-formulated combination of ingredients derived wholly from naturally-occurring foods, including specially formulated combinations of jalapeno peppers, bell peppers, garlic, almonds, lemons, and vinegar. Such formulations have been found to attenuate the duration and severity of common cold symptoms without jeopardizing the health and well-being of individuals suffering from diabetes and other medical conditions sensitive to blood pressure and to blood sugar fluctuations. These food supplement formulations afford diabetic patients regimen for treating common cold symptoms, and for simultaneously sustaining safe blood pressure and blood sugar equilibrium.

8 Claims, No Drawings

COLD-REMEDY FOOD SUPPLEMENT FOR SIMULTANEOUSLY LOWERING BLOOD PRESSURE AND SUSTAINING BLOOD SUGAR

RELATED APPLICATIONS

This application claims priority based upon Provisional U.S. Application Ser. No. 60/819,682 filed Jul. 10, 2006.

FIELD OF THE INVENTION

This invention relates to food supplement compositions, and more particularly, relates to dietary food supplement compositions which promote the ability to quell adverse common cold symptoms while simultaneously reducing blood pressure and sustaining blood sugar equilibrium.

BACKGROUND OF THE INVENTION

It is common practice for people suffering from common colds to seek economical and effective over-the-counter remedies to cope with a plethora of adverse symptoms. Such symptoms may include sore throat, laryngitis, sneezing, nasal congestion, nasal mucous drainage, tearing, fever, headache, and the like. Unfortunately, such readily available remedies may affect blood pressure and blood sugar level. Accordingly, cold-sufferers who must carefully control blood pressure and/or blood sugar level may be foreclosed for health reasons from availing themselves of such remedies. Most medicines which are prescribed to attenuate or eliminate symptoms attributable to the common cold or the like typically fail to address concomitant adverse affects upon patients' blood pressure and blood sugar.

There appears to be a paucity of remedies, doctor-prescribed medicines or over-the-counter remedies for helping patients prevent the onset of the common cold or for quelling the symptoms associated with the common cold, and simultaneously controlling blood pressure and blood sugar equilibrium. It will be appreciated by those skilled in the art that, for patients having compromised blood pressure and/or blood sugar conditions, it is imperative that their blood pressure and/or blood sugar level not be adversely affected by any other health-related treatment—attributable to either medicine or dietary food supplement.

Indeed, in addition to such cold remedies—either obtained from doctors' prescriptions or from over-the-counter food supplements—for patients suffering from diabetes, having access to an over-the-counter food supplement that sustains permissible blood sugar levels significantly improves such patients' health and quality of life. A similar benefit is attributable to patients having abnormal blood pressure: having access to an over-the-counter food supplement that sustains permissible blood pressure.

Accordingly, these limitations and disadvantages of the prior art are overcome with the present invention, wherein improved compositions are provided which are particularly useful for enabling common cold symptoms to be prevented or assuaged without adversely affecting blood pressure and blood sugar equilibrium, and for sustaining blood pressure and blood sugar equilibrium.

SUMMARY OF THE INVENTION

The present invention provides food supplement compositions specially formulated for allaying symptoms associated with the common cold, and for simultaneously reducing blood pressure and for controlling blood sugar level. More particularly, compositions taught by the present invention comprise essentially ingredients derived wholly from naturally-occurring foods, and attenuate the duration and severity of common cold symptoms without jeopardizing the health and well-being of individuals suffering from diabetes and other medical conditions sensitive to blood pressure and to blood sugar fluctuations.

As will be hereinafter described, individuals who subscribe to a regimen of suitable daily doses of embodiments of the present invention tend to regularly enjoy significant health benefits. Embodiments taught hereunder are comprised of a synergistic combination of naturally-occurring food ingredients that not only attenuate and even eliminate recurring common cold symptoms, but also sustain preferred blood pressure and blood sugar equilibrium. It should be clearly understood, however, that embodiments hereof are not intended to alter a patient's established medication regimen which has been prescribed by qualified medical personnel. On the contrary, embodiments taught hereunder are intended only to supplement such a pre-established medication regimen in conjunction with an appropriate program of recurring daily exercise or like beneficial activities.

According to the teachings of the present invention, food supplement compositions have been discovered which enable persons to conveniently and routinely quell the various adverse symptoms associated with common colds. Moreover, these food supplement compositions afford diabetic patients and the like a particularly effective regimen for minimizing the onset of common cold symptoms, and for sustaining preferred blood pressure levels and blood sugar equilibrium.

It is an advantage of the present invention that food supplement compositions are provided to afford the human body extraordinary defenses for minimizing the severity and duration of common cold symptoms and for simultaneously sustaining blood pressure levels and blood sugar equilibrium.

It is an object and feature of the present invention to provide food supplement compositions that tend to simultaneously reduce blood pressure and sustain blood sugar level while assuaging the adverse affects associated with common colds.

These and other objects and features of the present invention will become apparent from the following detailed description, wherein reference is made to illustrative examples and related tables indicative of experimental results of embodiments hereof.

DETAILED DESCRIPTION

Remedial food supplement compositions contemplated by the present invention comprise a combination of naturally-occurring food recipes which have been formulated to quell common cold symptoms. It has been discovered that an individual's timely commencing a daily regimen of a suitable food supplement embodiment hereof may prevent the individual from acquiring common cold symptoms. Moreover, formulations taught by the present invention afford high-blood-pressure patients and diabetics a convenient, reliable, and inexpensive means for safely preventing or attenuating common cold symptoms. As will be hereinafter explained, suitably formulated food supplement compositions of the present invention inherently tend to sustain a patient's medically-preferred blood pressure and blood sugar levels in conjunction with a pre-existing physician-prescribed regimen of medication and exercise.

It will be appreciated that compositions of the present invention comprise a specially formulated combination of jalapeno peppers, bell peppers, garlic, almonds, lemons, and vinegar. It has been found that combinations of these active ingredients contribute synergistically to allaying symptoms attributable to common colds and the like. Experimental results have shown that dosage of preferred food supplement embodiments should preferably be self-administered in tablespoon quantities by mouth, preferably twice daily. It has been found that, typically, a dose of one or two tablespoons should be taken—in the absence of water or other liquid drink—contemporaneously with breakfast and dinner. As will be elucidated hereinafter, neither water nor other liquid is prerequisite for lubricating purposes during ingestion of food supplement embodiments hereof.

Indeed, it has been found to be more effective if a food supplement embodiment is ingested alone—in tablespoon quantities. Testing has shown that advantageously formulated and prepared finely-divided slurries taught by the present invention inherently afford a preferred range of viscosities that are conducive to easy ingestion thereof by a self-administering patient. Best cold-symptom remedial results appear to be obtained if and when food supplement administration occurs either immediately prior or immediately after mealtime. When taken with meals, food supplement embodiments have occasionally tended to distort normal taste of select individual testers. Hence, ingesting a formulation contemporaneously with meals, albeit not necessarily simultaneously with the meals, accomplishes the profound benefits contemplated by the present invention without otherwise adversely affecting enjoyment of the meal, per se.

As will hereinafter be described, food supplement compositions of the present invention comprise a combination of the following naturally-occurring ingredients: jalapeno peppers, bell peppers, garlic, almonds, lemons, and vinegar.

Jalapeno Pepper

It has been discovered that incorporating jalapeno peppers of suitable potency and portion into food supplement compositions of the present invention contribute to the beneficial treatment contemplated hereunder. Practitioners in the art will readily appreciate that jalapeno or chile peppers vary significantly in intensity and, accordingly, should preferably be selected to impart the appropriate characteristics. For example, it is well known that jalapeno can impart an enjoyable "hot" character to food preparations. Thus, by judicious inclusion of jalapeno into embodiments of the present invention, intended positive affects upon an individual's irritated mucous membranes; inflamed eyes, nose, and/or throat; and the like may be achieved without any significant adverse affects.

Thus, it has been found that food supplement embodiments formulated with relatively mild jalapeno peppers afford the contemplated synergistic remedial impact. It has been found that embodiments hereof should preferably incorporate jalapeno peppers having light-to-medium green color in order to impart a "mild" contribution to formulations taught herein. Nevertheless, jalapeno peppers having darker green color may also be used, albeit tending to impart a stronger or "hotter" affect during ingestion. As will be hereinafter illustrated, formulations having preferably 8, but ranging from 7 to 10, very large mild jalapeno peppers have afforded contemplated remedial affects for alleviating common cold symptoms.

Once being properly selected, jalapeno peppers are thoroughly washed with water, then the stems are preferably removed, and the remaining jalapeno portions—including the seeds—are preferably incorporated into food supplement compositions.

Bell Pepper

It has also been found that bell pepper, and, more particularly, green bell pepper, affords a tangy taste and crunchy texture to the food supplement mix, and fosters the purposes contemplated by the present invention. Bell peppers are known to belong to the same species as jalapeno peppers, but bell peppers generally tend to be sweet. It is, of course, known that the variety of the bell pepper plant and the stage of ripeness determine the flavor and color. Green bell peppers tend to have a slightly bitter flavor, while red, orange, and yellow bell peppers tend to have a sweet and fruity flavor. Brightly-colored bell peppers, regardless of whether green, red, yellow, or orange, afford an excellent source of antioxidants through presence of vitamins A and C therein. Red bell pepper is generally indicative of mature green pepper, and affords about three times as much vitamin C as green bell pepper.

While green bell pepper is a preferred ingredient of food supplement embodiments taught herein, it should be understood that other varieties of bell peppers may be substituted. As will be described in the illustrative examples hereinafter, formulations preferably having 3, but ranging from 2 to 4, large, mild green peppers have been found to afford significant positive remedies for common cold symptoms.

As preparation for admixture with the other ingredients taught herein, the bell peppers should be thoroughly washed with water, the stems and seeds preferably removed, and then the remaining pepper portions should be incorporated into embodiment compositions.

Garlic

Garlic, preferably in the form of garlic cloves, has been discovered to contribute to the synergy afforded by food supplement embodiments of the present invention. Practitioners in the art will readily appreciate that garlic is widely regarded as constituting a healthy herb that is regularly recommended as a remedy for a diversity of ailments from the common cold to the flu, and even beyond. Raw garlic is known to be a natural antibiotic and antioxidant, and is believed to reduce blood pressure and blood sugar levels.

As will be described in the illustrative examples hereinafter, formulations preferably having 7, but ranging from 6 to 9, very large cloves of garlic have afforded positive remedies for common cold symptoms. Prior to be admixed with the other ingredients taught herein, garlic cloves or the like should be thoroughly wash with water, the outer peel preferably removed, and the remaining garlic clove portion should be incorporated into the food supplement mix.

Almonds

Almonds, preferably a combination of a major portion of shelled and skinned almonds in conjunction with a minor portion of unskinned almonds, contribute to the nutritional and remedial threshold taught by food supplement embodiments of the present invention. Whole almonds—skin included—are believed by practitioners in the food supplement art to provide a catalyst function for heightening antioxidant affects of Vitamin E. Almonds are also an especially advantageous ingredient for sustaining a patient's normal blood flow and for affording a patient protection against increasing blood pressure.

Almonds also impart to a patient the benefit of a experiencing a mellow, pleasing sensation during ingestion of food supplement compositions. Thus, almonds appear to neutralize and attenuate the otherwise burning sensation commonly experienced by patients or the like imbibing jalapeno peppers.

As will be described in the illustrative examples hereinafter, formulations having preferably about 65 natural almonds with skin, ranging from 55 to 75 almonds, and about 3 medium-large almonds with husk have afforded positive remedies for common cold symptoms. After being thoroughly washed with water, the almonds should be incorporated into the food supplement mix.

Lemons

Lemons are also added to food supplement embodiments of the present invention. It is well known that lemon fruits afford an advantageous nutritional balance including Vitamins A and C, citric acid, ascorbic acid, calcium, phosphorus, and potassium. Sliced whole lemons, preferably 3, ranging from 2 to 4 medium-large lemons—including the peel—should be thoroughly wash with water and then incorporated into embodiments of the food supplement of the present invention.

Mints

As is common in the art, to promote a positive experience while being self-administered, mints should preferably be included in ingredient embodiments to provide a measure of mellow and familiar sweet taste and flavor. While there are many suitable hard candy mints that may be incorporated into food supplement embodiments, it has been found advantageous to use Brachs Starlight peppermints. In particular, preferably about 20 Starlight peppermints, ranging from 15 to 30 thereof, have been found to afford a pleasing taste and suitable consistency.

Vinegar

It is well known that vinegar is basically a sour-tasting liquid that obtains from oxidation of ethanol in fermented fruit juice, apple cider, wine, beer, and, indeed, in most alcohol-containing liquids. White or clear vinegar is a common variety, while cider vinegar obtains from apple cider. It has been discovered that ordinary white vinegar tends to raise blood pressure; accordingly, preferred food supplement embodiments are comprised of apple cider vinegar in the range 28 to 36 ounces. To obtain the most preferred consistency and performance contemplated hereunder, 32 ounces of apple cider vinegar should be used.

Mixing Procedure

While alternative procedures have been found to be effective for preparing food supplements as contemplated hereunder, it has been found to be particularly effective to prepare embodiments of the present invention via essentially a five-step procedure. This procedure commences with preferably thoroughly water-washing the plurality of substantially solid ingredients corresponding to natural fruits and vegetables. Then, ether in turn or sequentially, this plurality of washed ingredients is separated from the wash water and left in a substantially water-free condition. Next, these water-free ingredients are vigorously blended until a finely-divided paste is formed. It will be appreciated that this paste-like consistency is attributable to a dispersion of finely-divided fruit and vegetable particles in their natural juices and the like. This paste is then admixed with vinegar to form a slurry, and moderately and slowly boiled to again form a paste-like consistency. This boiled paste is next cooled slowly at room temperature to yield finished food supplement.

More particularly, the preferred preparation protocol of the present invention comprises the five steps of:

Step 1: Washing

Thoroughly washing the plurality of substantially solid fruits and vegetables, e.g., jalapeno peppers, bell peppers, garlic, almonds and lemon, with water. Of course, such washing may be achieved by emplacing such plurality of fruits and vegetables in a conventional suitably-sized colander or the like and flushing with streaming water. The selected fruits and vegetables may be washed all at once or sequentially; thorough washing thereof is advantageous for health and safety reasons. Thus, the presence of residual pesticides or other potentially harmful chemicals and contaminants is to be avoided. It will be appreciated that the spent wash-water must be isolated from the washed ingredients of the present invention.

Step 2: Blending

After being isolated from contaminants or the like, the jalapeno peppers, bell peppers, garlic cloves, almonds, and lemon ingredients should preferably be admixed with the mints in vinegar liquid to form a slurry. It has been found to be advantageous for this slurry of solid and liquid ingredients to be blended by preferably high-intensity agitation for at least three minutes; more preferably, this blending should continue for five to ten minutes until this slurry has become populated by finely divided solid ingredients. It should be apparent that blending will vary depending upon the conventional blender, food processor, or the like used to effectuate the intended agitation; nevertheless, agitation should persist until the prerequisite slurry attributes have been achieved.

Step 3: Slurry Formation The slurry is then removed from the blender and transferred to a suitably-sized pot. Care should be taken that all of the particles residing on the side walls and bottom of the blender or the like are removed and poured into the pot. Such residual particulate fruits and vegetables may be conveniently flushed therefrom by rinsing with all or a portion of the liquid ingredient, thereby forming a slurry. It has been found to be particularly advantageous to prepare preferred slurry formulations with the liquid component comprising about 32 ounces of commercially-available apple cider vinegar; it should be understood that this apple vinegar component can range from about 28 to 36 ounces to form a slurry of ingredients contemplated hereunder.

Step 4: Cooking The slurry is then boiled in the pot for about 8 minutes with constant stirring to avoid burning or scorching of the slurry. A conventional spatula has been found to be especially effective for assuring circulation of the slurry to avoid protracted contact with the hot pot surfaces during cooking. It has been found that consistent satisfactory results have been achieved by first bringing the mixture to a rapid-boil under a high level of heating and then, once boiling has been achieved, to reduce the heat source to a medium level sufficient to sustain boiling. Boiling should be moderated so as to engender a thick liquid paste, but not a viscous paste. Preferred food supplement embodiments should be characterized by liquid paste consistency which may be easily self-administered by tablespoon without the need for any accompanying water or other common liquid drink-lubricant that enables pills, tablets, caplets and the like to be expeditiously ingested by mouth.

Step 5: Cooling The mixture is then cooled within the same pot; the pot should be covered and preferably air-cooled. It will be appreciated that covering the pot during cooling prevents evaporation of the liquid component thereby undermining the preferred viscosity of the resultant food supplement. That is, if too much evaporation of vinegar and water occurs, the viscosity of the slurry tends to increase whereby it tends to become too thick for ingestion as contemplated hereunder, i.e., ingestion without using water or the like. This controlled cooling should continue until the mixture reaches room temperature.

As an illustration of preparation variations of embodiments of the present invention, an alternative blending procedure (Step 2) is to admix vinegar after the solid fruit and vegetable ingredients have been thoroughly washed. Then, once all of these prescribed ingredients have been admixed, agitation thereof proceeds until a finely-divided slurry has been obtained. It will be understood that, since the resultant slurry is thinner than a slurry obtained when liquid is not admixed with the plurality of solid ingredients, there are minimal particles residing on the side walls and bottom of the blender or the like; notwithstanding, any such residual particulate fruits and vegetables should be flushed therefrom.

Food Supplement Administration

Viscosity

It is contemplated that food supplement embodiments should preferably be in the form of a thick liquid that is convenient to administer via tablespoon or the like. Dosage should preferably constitute one or two tablespoons which are preferably self-administered twice daily. It has been found that an administration regimen of once in the morning and once in the evening engenders remedial results contemplated herein. As any food supplement, embodiments of the present invention should not affect patients' or cold-sufferers' normal dietary and exercise regimens. That is, as should evident to those skilled in the art, any food supplement is designed to augment patients' pre-existing doctor-prescribed medication regimen and such patients' pre-existing health and fitness exercise regimen.

Food supplements of the present invention have been formulated and prepared to sustain a viscosity commensurate with readily being swallowed by patients. Accordingly, such food supplements should be individually self-administered slowly and then should be swallowed immediately. Neither water nor any other liquid is recommended or necessary for self-administering a formulation of the present invention. Once such food supplement has been swallowed as contemplated hereunder, water and other liquids may be imbibed at patients' discretion.

Recipe for Preferred Embodiment

This is a tabulation of the natural ingredients comprising the preferred embodiment of the food supplement formulation taught by the present invention:

| # | Ingredient | Qty (oz.) | % | Comments |
|---|---|---|---|---|
| 1 | Garlic Cloves | 5 | 4.4 | |
| 2 | Jalapeno Peppers | 20 | 17.5 | including core & seeds |
| 3 | Bell Peppers | 34 | 30.0 | including core & seeds |
| 4 | Lemons | 10 | 9.0 | including peel & seeds |
| 5 | Peppermint | 7 | 6.0 | |
| 6 | Almonds | 6 | 5.3 | |
| 7 | Apple Cider Vinegar | 32 | 28.0 | 2 cup (16-oz. size) |
| | Total | 114 | 100 | |

Test Results

The preferred embodiment was tested by diabetic patients and by patients otherwise suffering from blood sugar and blood pressure equilibrium deficiencies. As hereinbefore described, embodiments of the present invention seek to enable such patients to self-administer food supplement formulated not only for preventing or assuaging symptoms associated with common colds and the like, but also for controlling blood sugar and blood pressure within established healthy and safe limits.

Testing protocol consisted of a diversity of patients supplementing doctor-prescribed medication with the preferred embodiment. As hereinafter described, exemplary testing during successive two-week periods is represented for such patients who have supplemented normal self-administered protocol of prescribed medications with a composition taught by the present invention.

TEST I: Patient "BR" taking Normally Prescribed Medications and Food Supplement

A diabetic patient (identified as Patient "BR") supplemented her doctor-prescribed medication regimen for treatment of her blood sugar level and her blood pressure. She self-administered the preferred embodiment having the ingredients as enumerated herein. Table I shows one week's experimental results:

TABLE I

Patient BR: Medication Augmented with Food Supplement

| | Blood Sugar Level (mg/dl) | | | | Blood Pressure |
|---|---|---|---|---|---|
| | Breakfast | | Dinner | | |
| Day | Before | After | Before | After | High/Low |
| 1 | 150 | 172 | 138 | 149 | 146/83 |
| 2 | 168 | 169 | 141 | 158 | 140/87 |
| 3 | 155 | 234 | 152 | 164 | 147/77 |
| 4 | 154 | 237 | 148 | 149 | 160/90 |
| 5 | 191 | 193 | 154 | 193 | 154/84 |
| 6 | 122 | 219 | 155 | 217 | 164/92 |

The blood sugar medication was self-administered twice daily, at breakfast and dinner. The blood pressure medication was self-administered once daily. This medication was supplemented with two-tablespoon doses of the preferred embodiment which were self-administered twice daily, once in the morning and once in the evening. Patient BR's blood sugar level increased after meals: it is seen to have increased from only 1-2 mg/dl to about 80-100 mg/dl after breakfast; and from only 1 mg/dl to as much as about 40-60 mg/dl after dinner.

More particularly, for the second and fifth days of this week, the blood sugar increase was only 1-2 mg/dl after breakfast; on the third and fourth days, the blood sugar increase was at about 80 mg/dl; on the first day, the blood sugar increase was about 20 mg/dl and on the sixth day, the blood sugar increased to about 100 mg/dl.

Similarly, for the first, second, and third days of this week, the blood sugar increase was at least 11 mg/dl and as high as 17 mg/dl after dinner; on the fifth day, the blood sugar increase was about 40 mg/dl and on the sixth day, it increased to as much as about 60 mg/dl; and on the fourth day, the blood sugar increase was only 1 mg/dl.

For this patient's blood pressure pattern, her high blood pressure varied from 140 to 164. Her low blood pressure varied from 77 to 92.

TEST II: Patient BR taking Only Prescribed Medications

Patient BR exclusively sustained her doctor-prescribed medication for treatment of her blood sugar level and her blood pressure. No food supplement was taken. These observations were made during the week immediately following her combined medication and food supplement regimen per Test I (enumerated in Table I).

TABLE II

Patient BR: Medication Only

| | Blood Sugar Level (mg/dl) | | | | |
|---|---|---|---|---|---|
| | Breakfast | | Dinner | | Blood Pressure |
| Day | Before | After | Before | After | High/Low |
| 1 | 126 | 146 | 160 | 178 | 142/72 |
| 2 | 145 | 193 | 134 | 177 | 150/85 |
| 3 | 150 | 167 | 157 | 226 | 156/93 |
| 4 | 156 | 196 | 144 | 175 | 142/84 |
| 5 | 149 | 152 | 160 | 219 | 155/82 |
| 6 | 140 | 179 | 130 | 192 | 159/83 |
| 7 | 150 | 170 | 141 | 180 | 166/92 |

The blood sugar medication was self-administered twice daily, at breakfast and dinner. Predictably, the blood sugar level increases after meals, and, for Patient BR, is seen to increase from only 3 mg/dl to about 50 mg/dl after breakfast; and from about 20 mg/dl to as much as about 70 mg/dl after dinner.

More particularly, for the first, third, and seventh days of this week, the blood sugar increase was about 20 mg/dl after breakfast; on the second, fourth, and sixth days, the blood sugar increase was at least 39 mg/dl and as much as 48 mg/dl.

Similarly, for the third, fifth, and sixth days of this week, the blood sugar increase was at least 59 mg/dl and as high as 69 mg/dl after dinner; on the second, fourth, and seventh days, the blood sugar increase was at least 31 mg/dl and as much as 43 mg/dl; and on the first day, the blood sugar increase was only about 20 mg/dl.

The blood pressure medication was self-administered once daily. The high blood pressure varied from 142 to 166. The low blood pressure varied from 72 to 93.

TEST III: Patient "HM" taking Prescribed Medications and Food Supplement

Diabetic patient (identified as Patient "HM") supplemented his doctor-prescribed medication regimen for treatment of his blood sugar level and his blood pressure, with administration of the preferred embodiment having the ingredients enumerated herein. Table III shows one week's experimental results:

TABLE III

| | Blood Sugar Level (mg/dl) | | | | | |
|---|---|---|---|---|---|---|
| | Breakfast | | Lunch | | Dinner | Blood Pressure |
| Day | Before | After | Before | After | Before | After | High/Low |
| 1 | 109 | 148 | 124 | 187 | 132 | 129 | 138/68 |
| 2 | 117 | 152 | 124 | 191 | 123 | 120 | 126/70 |
| 3 | 116 | 143 | 141 | 274 | 120 | 123 | 128/76 |
| 4 | 116 | 161 | 147 | 254 | 88 | 142 | 132/78 |
| 5 | 98 | 128 | 124 | 208 | 106 | 162 | 132/68 |
| 6 | 106 | 171 | 135 | 131 | 109 | 177 | 130/58 |
| 7 | 115 | 162 | 89 | 100 | 114 | 168 | 134/72 |

The blood sugar medication (Glyburide) was self-administered twice daily, at breakfast and dinner. The blood pressure medication was self-administered once daily. This medication was supplemented with one-tablespoon doses of the preferred embodiment which were self-administered thrice daily, after each of breakfast, lunch, and dinner. Patient HM's blood sugar level increased after meals: it is seen to have increased from about 30 mg/dl to about 50-65 mg/dl after breakfast; from about 10 mg/dl to about 60-130 mg/dl after lunch; and from 3 mg/dl to as much as about 50-60 mg/dl after dinner.

More particularly, for the second, third, and fifth days of this week, the blood sugar increase was about 35 mg/dl after breakfast; on the first, fourth, and seventh days, the blood sugar increase was at about 40 mg/dl; on the sixth day, the blood sugar increase was as high as 65 mg/dl.

After lunch, for the first and second days of this week, the blood sugar increase was about 65 mg/dl; on the fourth and fifth days, the blood sugar varied from about 85 mg/dl to 100 mg/dl; on the third day, the blood sugar increase was about 130 mg/dl; on the sixth day, it had a slight decrease about 5 mg/dl; and on the seventh day, the blood sugar increase was about 10 mg/dl.

Similarly, after dinner, for the forth, fifth, sixth, and seventh days of this week, the blood sugar increase was about 55-65 mg/dl; and on the first three days, the blood sugar tended to remain the same, with there being a modes increase of 3 mg/dl on the third day and a modes decrease of 3 mg/dl on the first and second days.

For Patient HM's blood pressure pattern, his high blood pressure varied from 126 to 138. His low blood pressure varied from 58 to 78.

TEST IV: Patient HM taking Only Prescribed Medications

Diabetic Patient HM exclusively took his doctor-prescribed medication regimen for treatment of his blood sugar level and his blood pressure, without administration of a food supplement taught by the preferred invention. Table IV shows one week's experimental results:

TABLE IV

| | Blood Sugar Level (mg/dl) | | | | | |
|---|---|---|---|---|---|---|
| | Breakfast | | Lunch | | Dinner | Blood Pressure |
| Day | Before | After | Before | After | Before | After | High/Low |
| 1 | 115 | 156 | 121 | 254 | 120 | 166 | 144/78 |
| 2 | 110 | 180 | 146 | 163 | 163 | 174 | 146/84 |
| 3 | 118 | 158 | 163 | 168 | 104 | 97 | 142/84 |
| 4 | 111 | 162 | 138 | 218 | 107 | 172 | 144/66 |
| 5 | 110 | 153 | 124 | 253 | 128 | 151 | 130/70 |
| 6 | 122 | 142 | 126 | 167 | 86 | 179 | 150/76 |

TABLE IV-continued

| | Blood Sugar Level (mg/dl) | | | | | | Blood Pressure |
|---|---|---|---|---|---|---|---|
| | Breakfast | | Lunch | | Dinner | | |
| Day | Before | After | Before | After | Before | After | High/Low |
| 7 | 133 | 154 | 123 | 108 | 134 | | 144/78 |

The blood sugar medication (Glyburide) was self-administered twice daily, at breakfast and dinner. The blood pressure medication was self-administered three times daily. No food supplement augmented this regimen. Patient HM's blood sugar level increased after meals: it is seen to have increased from about 20 mg/dl to about 50 mg/dl after breakfast; from about 10 mg/dl to about 60-130 mg/dl after lunch; and from about mg/dl to about 50 mg/dl after dinner.

More particularly, for the first, third, and fifth days of this week, the blood sugar increase was about 40 mg/dl after breakfast; on the second and fourth days, the blood sugar increase was about 70 and 40 mg/dl, respectively; and on the sixth and seventh days, the blood sugar increase was about 20 mg/dl.

After lunch, for the first and fifth days of this week, the blood sugar increase was about 130 mg/dl; on the second day, the blood sugar increase was 17 mg/dl; on the third day, the blood sugar increase was only 5 mg/dl; on the seventh day, it had a decrease of about 25 mg/dl; and on the fourth and sixth days, the blood sugar increase was about 80 and 40 mg/dl, respectively.

Similarly, after dinner, for the first and fourth days of this week, the blood sugar increase was about 50-65 mg/dl; on the fifth and sixth days, the blood sugar increase was about 20 and 80 mg/dl, respectively; and on the second and third days, the blood sugar tended to remain the same, with there being a modes increase of about 10 mg/dl on the second day and a modes decrease of about 5 mg/dl on the third day.

For Patient HM's blood pressure pattern, his high blood pressure varied from 130 to 150, with this blood pressure tending to reach 144. His low blood pressure varied from 66 to 84, but tending to remain at less than 80.

TEST V: Patient MJ taking Prescribed Medications and Food Supplement

Diabetic patient (identified as Patient "MJ") supplemented his doctor-prescribed medication regimen for treatment of his blood sugar level and his blood pressure, with administration of the preferred embodiment having the ingredients enumerated herein. Table V shows one week's experimental results:

TABLE V

| | Blood Sugar Level (mg/dl) | | | | | | Blood Pressure |
|---|---|---|---|---|---|---|---|
| | Breakfast | | Lunch | | Dinner | | |
| Day | Before | After | Before | After | Before | After | High/Low |
| 1 | 113 | 126 | 124 | 128 | 120 | 129 | 160/80 |
| 2 | 120 | 131 | 118 | 122 | 121 | 128 | 148/95 |
| 3 | 116 | 121 | 127 | 129 | 200 | 148 | 146/85 |
| 4 | 130 | 131 | 101 | 110 | 122 | 124 | 122/80 |
| 5 | 132 | 134 | 107 | 118 | 123 | 126 | 160/80 |
| 6 | 128 | 127 | 120 | 122 | 118 | 124 | 150/75 |
| 7 | 107 | 119 | 122 | 131 | 116 | 128 | 163/76 |

The blood sugar medications (Metformin and Glyburide) were self-administered twice daily, at breakfast and dinner. The blood pressure medication was self-administered also twice daily. These medications were supplemented with one-tablespoon doses of the preferred embodiment which were self-administered thrice daily, after each of breakfast, lunch, and dinner. Patient MJ's blood sugar level generally increased after meals.

More particularly, for the first, second, and seventh days of this week, the blood sugar increase was about 12 mg/dl after breakfast; on the third and fifth days, the blood sugar increase was about 5 mg/dl; on the fourth and sixth day, the blood sugar increase was virtually unchanged, being only 1 mg/dl and then actually decreased by 1 mg/dl.

Similarly, after lunch, for the first, second, third, and sixth days of this week, the blood sugar increase was about 2-4 mg/dl; on the fourth, fifth, and seventh days, the blood sugar was about 9 mg/dl.

Similarly, after dinner, for the first and seventh days of this week, the blood sugar increase was about 10 mg/dl; for the second and sixth days of this week, the blood sugar increase was about 6 mg/dl; and on the fourth and fifth days, the blood sugar increase was about 3 mg/dl.

For Patient MJ's blood pressure pattern, his high blood pressure varied from 122 to 163. His low blood pressure varied from 75 to 95.

TEST VI: Patient MJ taking Only Medications

Diabetic Patient MJ exclusively took his doctor-prescribed medication regimen for treatment of his blood sugar level and his blood pressure, without administration of a food supplement taught by the preferred invention. Table VI shows one week's experimental results:

TABLE VI

| | Blood Sugar Level (mg/dl) | | | | | | Blood Pressure |
|---|---|---|---|---|---|---|---|
| | Breakfast | | Lunch | | Dinner | | |
| Day | Before | After | Before | After | Before | After | High/Low |
| 1 | 150 | 161 | 147 | 156 | 162 | 181 | 170/69 |
| 2 | 183 | 191 | 141 | 171 | 161 | 184 | 171/75 |
| 3 | 201 | 215 | 171 | 204 | 163 | 192 | 160/80 |
| 4 | 148 | 161 | 169 | 184 | 192 | 199 | 165/75 |
| 5 | 171 | 190 | 186 | 191 | 188 | 191 | 165/85 |
| 6 | 164 | 181 | 190 | 200 | 190 | 197 | 160/80 |
| 7 | 179 | 186 | 180 | 182 | 186 | 189 | 165/95 |

The blood sugar medications (Metformin and Glyburide) were self-administered twice daily, at breakfast and dinner. The blood pressure medication was self-administered three times daily. No food supplement augmented this regimen. Patient MJ's blood sugar level increased after meals: it is seen to have increased from about 20 mg/dl to about 50 mg/dl after breakfast; from about 10 mg/dl to about 60-130 mg/dl after lunch; and from about 10 mg/dl to about 50 mg/dl after dinner.

More particularly, for the first, third, and fifth days of this week, the blood sugar increase was about 40 mg/dl after breakfast; on the second and fourth days, the blood sugar increase was about 70 and 40 mg/dl, respectively; and on the sixth and seventh days, the blood sugar increase was about 20 mg/dl.

After lunch, for the first and fifth days of this week, the blood sugar increase was about 130 mg/dl; on the second day, the blood sugar increase was 17 mg/dl; on the third day, the blood sugar increase was only 5 mg/dl; on the seventh day, it had a decrease of about 25 mg/dl; and on the fourth and sixth days, the blood sugar increase was about 80 and 40 mg/dl, respectively.

Similarly, after dinner, for the first and fourth days of this week, the blood sugar increase was about 50-65 mg/dl; on the fifth and sixth days, the blood sugar increase was about 20 and 80 mg/dl, respectively; and on the second and third days, the blood sugar tended to remain the same, with there being a modes increase of about 10 mg/dl on the second day and a modes decrease of about 5 mg/dl on the third day.

For Patient MJ's blood pressure pattern, his high blood pressure varied from 160 to 171, with this blood pressure tending to remain at about 165. His low blood pressure varied from 75 to 95.

Recap

Experience teaches that during various successions of 2-week periods wherein prescribed medications were supplemented with the preferred embodiment, the food supplement compositions described herein appear to generally accommodate the remedial needs of a diversity of diabetic patients suffering from common cold symptoms. Such patients' cold-related symptoms appeared to be attenuated without adversely affecting either normally safe blood sugar levels or blood pressure equilibrium.

Hence, unlike the prior art, the present invention teaches food supplement compositions for remedying the common cold without disturbing both blood pressure and blood sugar equilibrium.

Other variations and modifications will, of course, become apparent from a consideration of the specific embodiments and illustrative examples and concomitant methodology herein before described. Accordingly, it should be clearly understood that the present invention is not intended to be limited by the particular disclosure, embodiments and formulation examples hereinbefore described, but that the present invention is to be measured by the scope of the appended claims herein.

What is claimed is:

1. A method for preparing a food supplement composition for quelling a patient's common cold symptoms while simultaneously lowering said patient's normal blood pressure and sustaining said patient's normal blood sugar level, said method comprising the steps of:
    selecting substantially solid fruits and vegetables comprising garlic cloves, bell pepper, jalapeno peppers, lemon, and almonds;
    said substantially solid fruits and vegetables consisting essentially of about 5 ounces of garlic cloves, about 34 ounces of bell pepper, about 20 ounces of jalapeno pepper, about 6 ounces of almonds, and about 10 ounces of lemon;
    water-washing said substantially solid fruits and vegetables and treating the water-washed fruits and vegetables by
    removing stems and seeds from said water-washed bell peppers;
    removing stems from said water-washed jalapeno peppers;
    slicing said water-washed lemons;
    removing outer shells from said water-washed almonds;
    removing outer peels from said water-washed garlic cloves;
    blending said treated fruits and vegetables with about 7 ounces of peppermint hard candies in about 32 ounces of vinegar to form a slurry;
    transferring slurry to a pot;
    cooking said transferred slurry in said pot with constant stirring to avoid burning or scorching thereof, and to form a liquid paste; and
    cooling said paste within said pot.

2. The method recited in claim 1, wherein said washing step comprises emplacing said substantially solid fruits and vegetables in a conventional suitably-sized colander and flushing with streaming water.

3. The method recited in claim 2, wherein said water-washing step comprises emplacing each substantially solid fruit and vegetable of said substantially solid fruits and vegetables in a conventional suitably-sized colander and individually flushing each said substantially solid fruit or vegetable with streaming water.

4. The method recited in claim 1, wherein said blending step comprises using apple cider vinegar liquid to form said slurry.

5. The method recited in claim 1, wherein said cooking step comprises boiling said transferred slurry in said pot for about 8 minutes.

6. The method recited in claim 1, wherein said transferring step comprises thoroughly removing all of said blended slurry so that there is substantially no residue left behind.

7. The method recited in claim 1, wherein said cooling step comprises air-cooling said liquid paste within said pot.

8. The method recited in claim 7, wherein said air-cooling step continues until said liquid paste reaches room temperature.

* * * * *